United States Patent
Kim et al.

(10) Patent No.: US 9,939,451 B2
(45) Date of Patent: Apr. 10, 2018

(54) BIOMARKER FOR DETECTING WHITE MATTER STROKE, CONTAINING TOLL-LIKE RECEPTOR 2, AND MEDICAL USE OF TOLL-LIKE RECEPTOR 2

(71) Applicant: AJOU UNIVERSITY INDUSTRY—ACADEMIC COOPERATION FOUNDATION, Suwon-si, Gyeonggi-do (KR)

(72) Inventors: Byung Gon Kim, Seoul (KR); Jun Young Choi, Suwon-si (KR)

(73) Assignee: AJOU UNIVERSITY INDUSTRY-ACADEMIC COOPERATION FOUNDATION, Suwon-si, Gyeonggi-do (KR)

( * ) Notice: Subject to any disclaimer, the term of this patent is extended or adjusted under 35 U.S.C. 154(b) by 0 days.

(21) Appl. No.: 14/766,759

(22) PCT Filed: Aug. 30, 2013

(86) PCT No.: PCT/KR2013/007825
§ 371 (c)(1),
(2) Date: Aug. 10, 2015

(87) PCT Pub. No.: WO2014/123288
PCT Pub. Date: Aug. 14, 2014

(65) Prior Publication Data
US 2016/0041189 A1    Feb. 11, 2016

(30) Foreign Application Priority Data
Feb. 8, 2013  (KR) .................. 10-2013-0014520

(51) Int. Cl.
| | |
|---|---|
| *G01N 33/53* | (2006.01) |
| *G01N 33/566* | (2006.01) |
| *G01N 33/68* | (2006.01) |
| *A61K 38/08* | (2006.01) |
| *C12Q 1/68* | (2018.01) |
| *A61K 38/14* | (2006.01) |
| *A61K 31/716* | (2006.01) |
| *A61K 31/739* | (2006.01) |

(52) U.S. Cl.
CPC ....... *G01N 33/6896* (2013.01); *A61K 31/716* (2013.01); *A61K 31/739* (2013.01); *A61K 38/08* (2013.01); *A61K 38/14* (2013.01); *C12Q 1/6883* (2013.01); *C12Q 2600/136* (2013.01); *C12Q 2600/158* (2013.01); *G01N 2500/04* (2013.01); *G01N 2800/2871* (2013.01)

(58) Field of Classification Search
None
See application file for complete search history.

(56) References Cited

U.S. PATENT DOCUMENTS

2012/0164159 A1  6/2012 Dellacasagrande

FOREIGN PATENT DOCUMENTS

KR   10-2012-0075457 A   7/2012

OTHER PUBLICATIONS

International Search Report for PCT/KR2013/007825 dated Nov. 12, 2013 from Korean Intellectual Property Office.
Okun et al., "Toll-like receptors in neurodegeneration" Brain Research Reviews, vol. 59, issue 2, pp. 278-292 (2009) See abstract; pp. 283-284, and figure 2.
Hayakawa et al., "High-mobility group box 1 from reactive astrocytes enhances the accumulation of endothelial progenitor cells in damaged white matter" Journal of Neurochemistry, vol. 125, issue 2, pp. 273-280 (published on online on Dec. 28, 2012) See the entire document.
Leung et al., "It's all in the family: multiple Toll-like receptors offer promise as novel therapeutic targets for stroke neuroprotection" Future Neurology, vol. 4, No. 2, pp. 201-208 (Mar. 2009) See the entire document.
Urra et al., "Monocytes Are Major Players in the Prognosis and Risk of Infection After Acute Stroke" Stroke, vol. 40, No. 4, pp. 1262-1268 (2009) See the entire document.
Marik et al., "Lesion genesis in a subset of patients with multiple sclerosis: a role for innate immunity?" Brain, vol. 130, No. 11, pp. 2800-2815 (2007) See the entire document.

*Primary Examiner* — Olga N Chernyshev
(74) *Attorney, Agent, or Firm* — Revolution IP, PLLC

(57) ABSTRACT

The present invention relates to a biomarker composition for detecting white matter stroke, the biomarker composition containing a toll-like receptor 2 (TLR2), and a medical use using the TLR2. The TLR2 can be used as a biomarker for white matter stroke by defending against ischemic demyelination and oligodendrocyte death, and when targeting the TLR2, ischemic white matter stroke can be treated or prevented.

1 Claim, 6 Drawing Sheets

BIOMARKER FOR DETECTING WHITE MATTER STROKE, CONTAINING TOLL-LIKE RECEPTOR 2, AND MEDICAL USE OF TOLL-LIKE RECEPTOR 2

CROSS REFERENCE TO PRIOR APPLICATIONS

This application is a National Stage Application of PCT International Patent Application No. PCT/KR2013/007825 filed on Aug. 30, 2013, under 35 U.S.C. § 371, which claims priority to Korean Patent Application No. 10-2013-0014520 filed on Feb. 8, 2013, which are all hereby incorporated by reference in their entirety.

TECHNICAL FIELD

The present invention relates to a biomarker for detecting white matter stroke, the biomarker including a toll-like receptor 2 (TLR2), and a medical of the TLR2.

BACKGROUND ART

Ischemic lesions associated with subcortical white matter occupy over 20% of all ischemic stroke types. Ischemic white matter lesion have markedly different clinical aspects including leukoaraiosis having few or no neurological deficit, localized white matter infarction causing hemiplegia/dysesthesia, and vascular dementia caused by repetitive ischemic injuries in subcortical white matter. Unlike a case associated with ischemic lesions occurring in the cortex, a speech disorder or severe memory impairment is known to be a rare case.

Demyelination and oligodendrocyte (OL) damages are prominent features of ischemic white matter injury, and thus ischemic OL damages after subcortical white matter injury are targets that have been considered as an important therapeutic strategy.

The only therapeutic agent for ischemic stroke that has been authorized so far a drug for reperfusion of a blood vessel. Most of therapeutic agents for ischemic stroke that have been attempted several times to undergo clinical trials served as drugs to prevent neuron apoptosis, and it is now in a difficult situation to develop therapeutic agents for white matter stoke that can defend against demyelination and OL damages.

Meanwhile, KR 2012-0075457 disclosed that inflammatory and autoimmune diseases can be treated by using an antibody to a toll-like receptor.

DETAILED DESCRIPTION OF THE INVENTION

Technical Problem

The present invention is to investigate a biomarker for developing a therapeutic agent for white matter stroke, the biomarker having the effect of defending against demyelination and oligodendrocyte (OL) damages, and to provide a medical use of the biomarker.

Technical Solution

To achieve the above technical problems, the present invention provides a biomarker composition for detecting white matter stroke, including a toll-like receptor 2 (TLR2).

In addition, the present invention provides a kit for diagnosing white matter stroke, including a toll-like receptor 2 (TLR2)-specific molecule.

The TLR2-specific molecule may be a monoclonal antibody, a polyclonal antibody, a substrate, a ligand, or a cofactor.

In addition, the present invention provides a method of providing information required for diagnosis of white matter stroke, the method including: detecting expression profiles of toll-like receptor 2 (TLR2) in a sample obtained from an individual suffering from white matter stroke; and comparing the detected expression profiles with expression profiles of TLR2 in a health control group.

In addition, the present invention provides a method of screening a therapeutic agent for white matter stroke, the method including treating a compound to prevent or treat white matter stroke; and determining extent of toll-like receptor 2 (TLR2) expression.

In addition, the present invention provides a pharmaceutical composition for preventing or treating white matter stroke, including a toll-like receptor 2 (TLR2) agonist as an active ingredient.

The TLR2 agonist has the effect of defending against ischemic demyelination and oligodendrocyte death, and may be selected from Pam3CSK4, zymosan, peptidoglycan, amorphous lipopolysaccharide, and lipoteichoic acid.

Advantageous Effects of the Invention

According to the present invention, the TLR2 performs a defensive role against ischemic demyelination and OL death, and thus may be applied to a biomarker for detecting white matter stroke. When targeting the TLR2, ischemic white matter stroke can be treated or prevented.

BEST MODE

Figure 1:
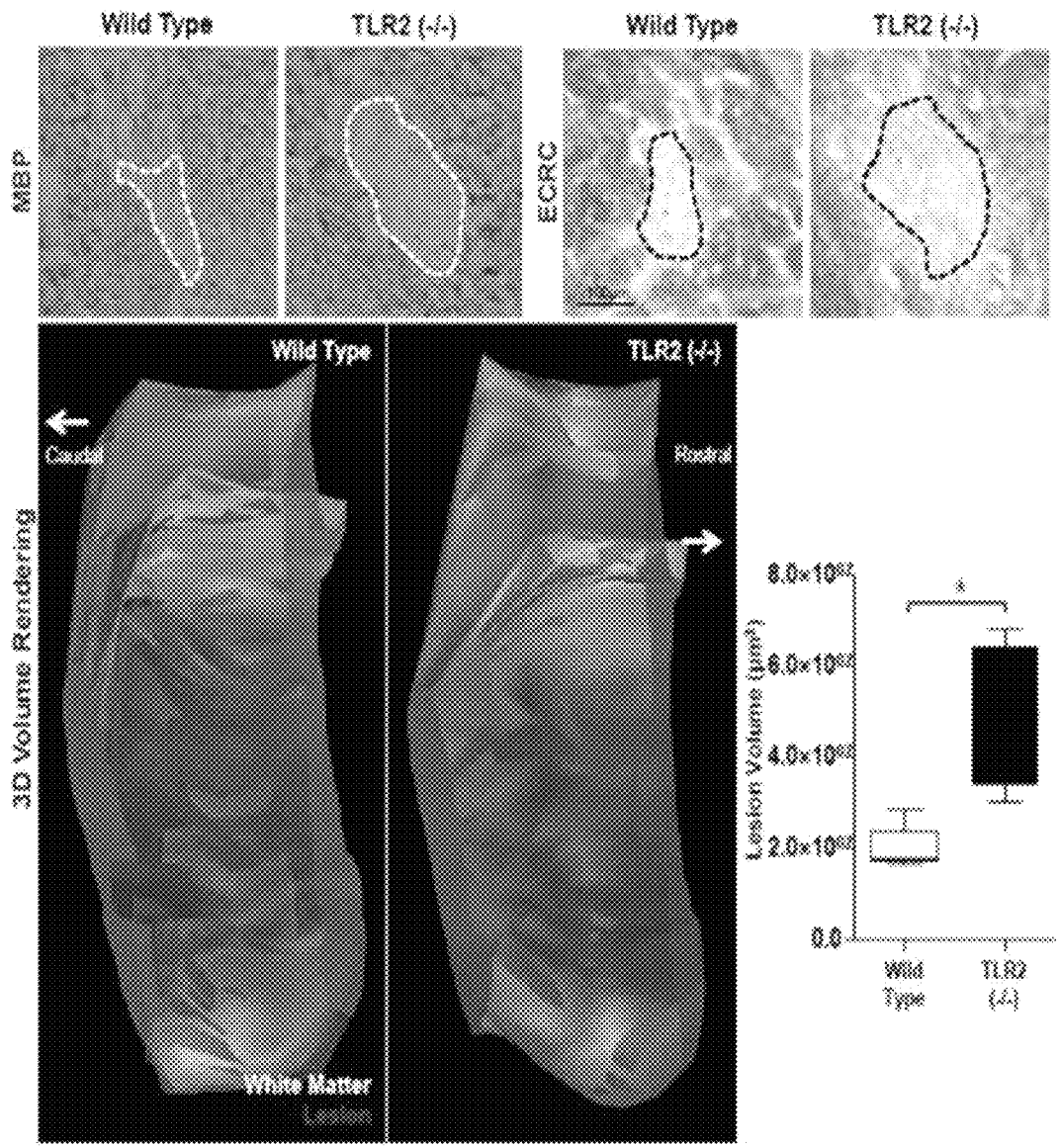
FIG. 1 shows the extent of endothelin-1 (ET-1)-induced ischemic demyelinated lesion in TLR2 knockout mice.

Hereinafter, the present invention will be described in detail.

The present inventor established a mouse model for studying white matter stroke by injecting endothelin-1 (ET-1) into the posterior limb of the internal capsule in a stereotactic manner, resulting in a localized demyelinating lesion at the injection site in the mouse model. It was also confirmed that the internal capsule was fully filled with activated macrophages, and infiltration of the activated macrophages increased the proinflammatory cytokine expression in the mouse model.

Meanwhile, toll-like receptor (TLR2), which is an upstream regulator of innate immunity, increases its amount in the ischemic demyelinating lesion after ischemic stroke. The extent of demyelinating pathology was markedly larger in a TLR2 knockout mouse (TLR2 (−/−) mouse) than that of a wild type (WT) mouse. In addition, the TLR2 (−/−) mouse showed more expression of activated caspase-3-positive oligodendrocytes (OL) than the WT mouse. In addition, the TLR2 (−/−) mouse showed decreased phosphorylation of ERK1/2, which is one of TLR2 downstream signaling proteins. In addition, OLs cultured from the TLR2 (−/−) mouse were more vulnerable to oxygen-glucose deprivation (OGD) than those cultured from the WT mouse. In addition, applying TLR2 agonists (e.g., Pam3CSK4) after OGD to the OLs cultured from the WT mouse substantially reduced OGD-induced OL death.

That is, the TLR2 may perform a defensive role against ischemic demyelination and OL death, and thus a therapeutic agent for ischemic white matter stoke can be developed by regulating the TLR2.

In this regard, the present invention provides a biomarker composition for detecting white matter stroke, including the TLR2.

Detection of the biomarker may be performed by directly detecting the presence of the biomarker proteins from human tissues or body fluids using two-dimensional electrophoresis, or indirectly detecting the presence of the biomarker proteins according to antigen-antibody reaction of contacting an antibody of the present invention with the human tissues or body fluids. Examples of the antigen-antibody reaction include immunoassay such as enzyme-linked immunosorbent assay (ELISA, Coated tube), magnetic particle methods using antibody-binding magnetic particles, latex particle methods using antibody-binding latex, or the like.

In addition, the present invention provides a kit for diagnosing white matter stroke, including a TLR2-specific molecule.

The TLR2-specific molecule may be a monoclonal antibody, a polyclonal antibody, a substrate, a ligand, or a cofactor, and preferably, may be a polyclonal antibody or a monoclonal antibody, and more preferably, may be a monoclonal antibody.

The polyclonal antibody may be prepared by injecting an immunogen, i.e., a biomarker protein or a fragment thereof, into a foreign host according to methods known to one of ordinary skill in the art. The foreign host may be a mammal including mice, rats, sheep, and rabbits. The immunogen injection may be performed by an intramuscular, intraperitoneal, or subcutaneous injection method. In general, to increase the antigenicity, the immunogen is injected with an adjuvant. Then, serum is regularly collected from the foreign host, and only serum showing improved potency and high specificity to the antigen may be collected or antibodies may be separated-purified therefrom.

The monoclonal antibody may be prepared by immortalized cell lines that are produced by fusion techniques known to one of ordinary skill in the art. For example, a mouse may be immunized with a biomarker protein or a synthetic peptide that is coupled with bovine serum albumin. Antigen-producing B lymphocytes separated from the mouse are fused with human or mouse myeloma, thereby generating an immortalized hybridoma. The hybridoma may be used for an indirect ELISA method to find out whether monoclonal antibodies are produced or not. Then, positive clones are selected and cultured to isolate and purify monoclonal antibodies. Alternatively, the hybridoma may be injected into the abdominal cavity of a rat, and then, ascites may be collected, thereby producing monoclonal antibodies.

In addition, the present invention provides a method of providing information required for diagnosis of white matter stroke, the method including: detecting expression profiles of TLR2 in a sample obtained from an individual suffering from white matter stroke; and comparing the detected expression profiles with expression profiles of TLR2 in healthy control group.

In addition, the present invention provides a method of screening a therapeutic agent for white matter stroke, the method including treating a compound with a sample obtained from an individual suffering from white matter stroke; and determining extent of TLR2 expression.

In addition, the present invention provides a pharmaceutical composition for preventing or treating white matter stroke, including a TLR2 agonist as an active ingredient.

The TLR2 agonist has the effect of defending against ischemic demyelination and oligodendrocyte death (OL death), and may be selected from Pam3CSK4, zymosan, peptidoglycan, amorphous lipopolysaccharide, and lipoteichoic acid.

The pharmaceutical composition according to the present invention may further include a suitable carrier, excipient, or diluent, each of which is conventionally used in the manufacture of a pharmaceutical composition in the art.

Examples of the suitable carrier, excipient, or diluents include lactose, dextrose, sucrose, sorbitol, mannitol, xylitol, erythritol, malitol, starch, acacia rubber, alginate, gelatin, calcium phosphate, calcium silicate, cellolose, methyl cellulose, microcrystalline cellulose, polyvinylpyrrolidone, water, methylhydroxybenzoate, propylhydroxybenzoate, talc, magnesium stearate, minieral oil, and the like.

The pharmaceutical composition may be formulated in the form of oral formulations, such as powders, granules, tablets, capsules, suspensions, emulsions, syrups, and aerosols, external applications, suppositories, and sterile injection solutions, according to methods know in the art.

When the pharmaceutical composition is formulated, typical diluents or excipients, such as fillers, extenders, binders, wetting agents, disintegrating agents, and surfactants, may be used. When preparing solid formulations for oral administration, the pharmaceutical composition may be formulated in the form of tablets, pills, powders, granules, or capsules. In addition, the solid formulations may be prepared by mixing with at least one excipient, such as starch, calcium carbonate, sucrose, lactose, or gelatin.

In addition to simple excipients, magnesium stearate or talc may be used as a lubricant. Liquid formulations for oral administration may include suspensions, solutions containing medicine, emulsions, or syrups. In addition to widely-used simple dilutents, such as water or liquid paraffin, various excipients, such as wetting agents, sweeteners, aromatics, or preservatives, may be included.

Formulations for parenteral administration may include sterilized solution, nonaqueous solvents, suspensions, emulsions, lyophilized preparations, or suppositories. Examples of the nonaqueous solvents or suspensions include propylene glycol, polyethylene glycol, vegetable oil, such as olive oil, or injectable esters, such as ethyl oleate. In addition, as a suppository base, witepsol, macrogol, tween 61, cacao butter, laurinum, or glycerogelatin may be used.

The amount of the active ingredient of the pharmaceutical composition may vary according to a patient's age, gender, body weight, drug administration route, severity of disease, and type of disease. The pharmaceutical composition may be administered once a day or up to several times a day. That is, dosage of the pharmaceutical composition, in any aspect, has no intention of limiting the scope of the present invention.

The pharmaceutical composition may be administered by a variety of routes in mammals, such as rats, mice, domestic animals, or humans. Such various administration routes are all expected, and for example, pharmaceutical composition may be administered by oral, rectal or intravenous, intramuscular, subcutaneous, intrauterine duramater or intracerebroventricular injection.

Hereinafter, one or more embodiments will be described in more detail with reference to the following examples. However, these examples are for illustrative purposes only and are not intended to limit the scope of the one or more embodiments.

MODE OF THE INVENTION

EXAMPLE 1

Preparation of Brain Tissue and Immunohistochemical Analysis

1) Animals and Surgical Procedures

An adult female C57BL/6 mouse and a TLR2-knock out mouse of C57BL/6 background, each weighing about 25 g to about 28 g, were used. The animal handling and surgical procedures were in accordance with the regulation set by Ajou University Institutional Animal Care and Use Committee. After performing anesthetization with chloral hydrate (400 mg/kg, intraperitoneal administration), animals were placed in a stereotactic frame, and then, craniectomy was made with a drill for placement of a 32-gauge needle into the right internal capsule to inject endothelin-1 (ET-1) to the animals (wherein the target coordinates were as follows: +1.0 from posterior to ventral; +2.8 mm from lateral to midline; +4.3 mm from dorsal to ventral; 20° angled to midline). Here, the 20° angulation was to prevent damages to the primary motor cortex, hippocampus, and cerebral ventricles. After ET-1 was injected to each animal, to prevent reverse flow, the needle was left in place for 10 minutes, and then, was slowly removed from the brain.

2) Tissue Processing and Immunohistochemical Analysis

After performing transcardiac perfusion with phosphate-buffered saline (PBS) in each animal, the animals were subjected to perfusion again with 4% paraformaldehyde dissolved in 0.1 M phosphate buffer (pH 7.4). Then, the brains were removed, post-fixed for about 2 hours, and then, immersed into sucrose solution at various concentrations. Coronal sections (20 μm) of each brain were cut using a cryostat (Leica CM3050S; Wetzlar, Germany) to series of 1:10. Then, coronal brain sections were placed on a SuperFrost Plus slide (Fisher Scientific, Pittsburgh, Pa.).

To quantify the area of demyelinated white matter, the coronal brain sections were stained with eriochrome cyanine. Then, the stained coronal brain sections were immerged in a staining solution for about 8 minutes, wherein the staining solution includes 230 ml of 0.2% eriochrome cyanine (ER) (Sigma) dissolved in 3% hydrochloric acid and 10 ml of 10% $FeCl_3 \cdot 6H_2O$ (Sigma). Afterwards, the coronal brain sections were washed using running tap water, and then, were differentiated in 1% aqueous $NH_4OH$.

For immunohistochemistry, the coronal brain sections were incubated overnight at a temperature of 4° C. with anti-NG2 (rabbit polyclonal; 1:200; Millipore), anti-APC-CC1 (mouse monoclonal; 1:200; Abcam), anti-MBP (rat monoclonal; 1:200; Abcam), anti-Iba-1 (rabbit polyclonal; 1:500; Wako), and anti-activated caspase 3 (rabbit polyclonal; 1:100; Millipore). The coronal brain sections were washed, and then, incubated at room temperature for 1 hour using appropriate biotinylated secondary antibodies or Alexa Fluor 488 or 594 tagged secondary antibodies (Molecular Probes, Eugene, Oreg.). For chromogenic analysis of the antigen-antibody reaction, a composite of avidin-biotinylated composite was formed for about 30 minutes, and then, the composite was cultured using a peroxidase substrate (DAB) until the reaction color was developed at a desirable strength. For fluorescence staining, a cover slip was placed on a slide having a glycerol-based mounting medium (Biomeda, Foster City, Calif.), and then, the medium was observed through Olympus confocal laser scanning microscope (FV 300, Tokyo, Japan).

As a result, it was confirmed that, as shown in FIG. 1, the size of the ET-1-induced ischemic demyelinating lesion was significantly bigger in the TLR2 knockout mouse than that in the wild type mouse.

EXAMPLE 2

Preparation of Primary OL Cultures and Reviews of OGD Effects

1) Preparation of Primary OL

Primary OL cultures were prepared from cortices of newborn C57BL/6 on postnatal day 0 (P0) to postnatal day 1 (P1), and/or TLR2 (−/−) mouse, according to the method reported in Journal of Visualized Experiment by O'Meara R. After 9-10 days in vitro, confluent mixed glial cultures were obtained. The mixed glial cultures were shaken at a temperature of about 37° C. for about 1 hour at a speed of about 200 rpm, so as to remove microglia. Afterwards, a second cycle of shaking was then performed at a temperature of about 37° C. for about 18 hours at a speed of about 250 rpm, so as to remove OLs from astrocyte monolayer. The cell suspensions obtained therefrom was plated on a bacterial grade Petri dish for about 1 hour to separate OLs from remaining microglia and astrocytes. Purified OLs were plated on a poly-D-lysine coated 12 well ($1.5 \times 10^5$ cells/well) or 96 well ($1.5 \times 10^4$ cells/well) or on a 9 mm coverslip ($1.0 \times 10^4$ cells/coverslip). The purified OL cultures obtained therefrom did not contain nerve cells nor astrocytes, and the purity of the OL cultures was at least about 95%.

2) Oxygen-Glucose Deprivation (OGD) and Drug Treatment

For OGD challenge, the purified OLs were cultured for about 1 day in a serum-free differentiation medium, washed with PBS three times, and then, transferred to an anaerobic chamber (Forma Scientific, Marietta, Ohio). Afterwards, the culture medium was replaced by a differentiation medium that did not contain serum and glucose, wherein the differentiation medium had been saturated with nitrogen gas for about 1 hour. The cells were exposed to OGD for about 2 hours, and then, transferred to a normoxic chamber. The medium was replaced again by a fresh medium containing glucose and Pam3CSK4 (1 μg/ml, invivogen), U0126 (10 μM, Calbiochem) and/or LY294002 (10 μM, Calbiochem).

3) Lactate Dehydrogenase (LDH) Analysis

For quantification of OGD-induced OL death, LDH assay was performed using an assay kit (Takara Bio, Inc., Madison, Wis.) to measure LDH generated in a bathing medium in association with damaged OL at 24 hours after the onset of OGD challenge. The LDH level corresponding to typical cell death was determined in sister cultures exposed 1.5% Triton X-100 for 24 hours (complete cell death, CD). Baseline (BL) LDH levels were determined in a condition of only medium without OLs. Percentage of cell death in each experimental condition was calculated using a following formula.

{% of OL death=(experimental value−BL)×100/(CD−BL)}

Figure 2:
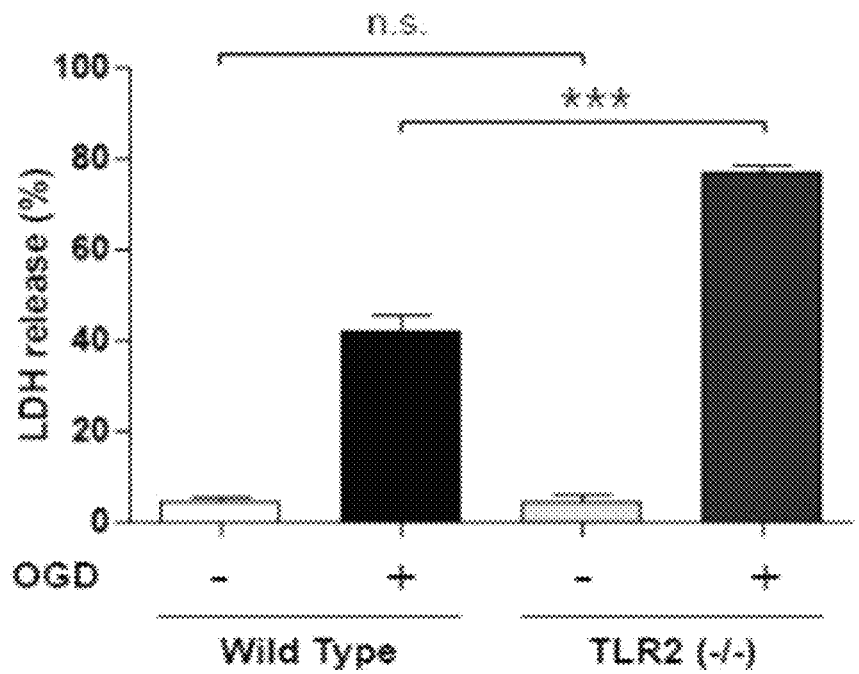
FIGS. 2 and 4 show the results obtained by lactate dehydrogenase (LDH) assay and TUNEL staining analysis, respectively, in regard to the effect of TLR2 to oxygen-glucose deprivation (OGD)-induced OL death.
Figure 3:
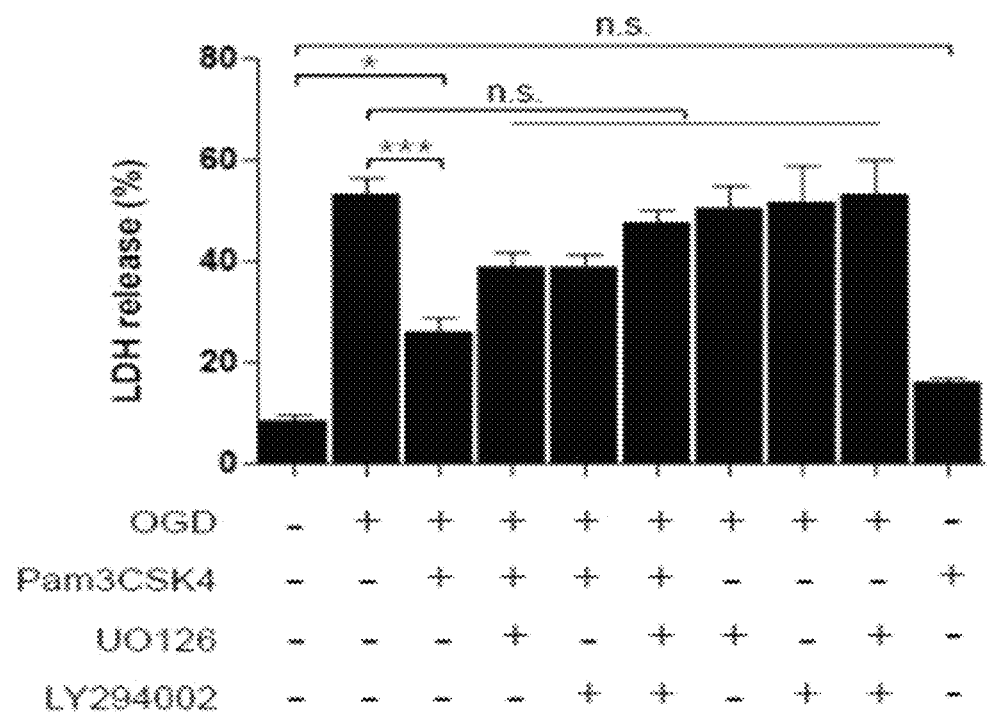
FIGS. 3 and 5 show the results obtained by LDH assay and TUNEL staining analysis, respectively, in regard to the effect of TLR2 agonist treatment to OGD-induced OL death.

As a result, it was confirmed that, as shown in FIG. 2, the OLs from the TLR2 knockout mouse showed significantly increased LDH release in accordance with OGD compared to those from the wild type mouse. That is, the OLs from the TLR2 knockout mouse were found to be more vulnerable to OGD than those from the wild type mouse. Meanwhile, as shown in FIG. 3, it was also confirmed that the treatment with TLR2 agonist, Pam3CSK4, reduced the extent of OGD-induced OL death.

4) Immunocytochemistry TUNEL Staining Analysis

To investigate OL death, purified OLs were grown on a 9 mm Aclar fluorocarbon cover slip coated with poly-D-lysine in an OL differentiation medium. The grown OLs were washed with PBS times, and then, fixed with 4% paraformaldehyde for 20 minutes. Then, the fixed OLs were subjected to TUNEL staining using an in situ apoptosis detection kit (ApopTag, Millipore).

Figure 4:
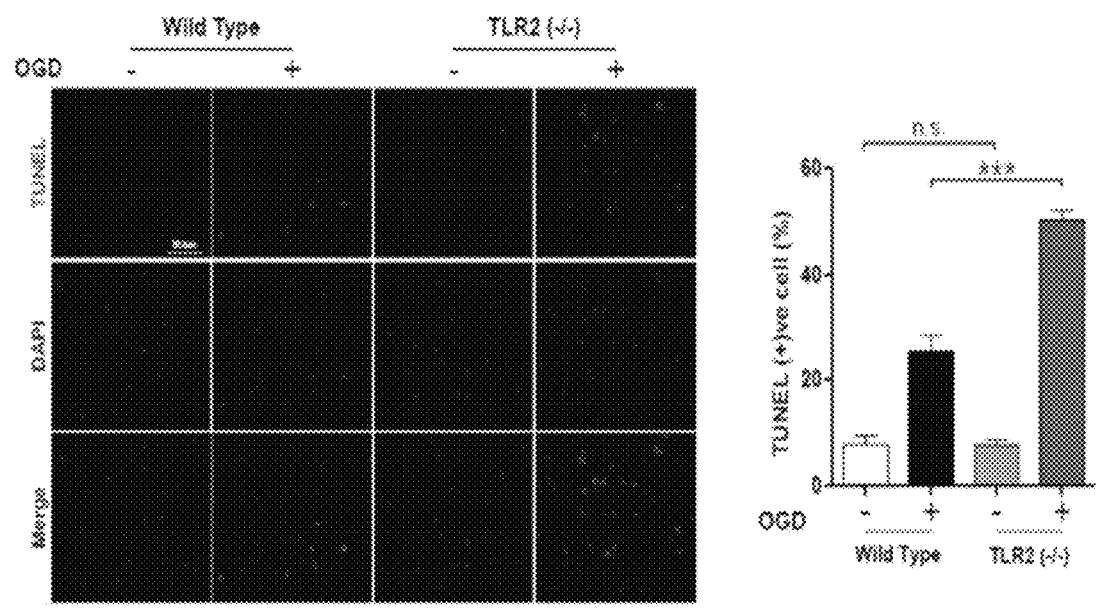
Figure 5:
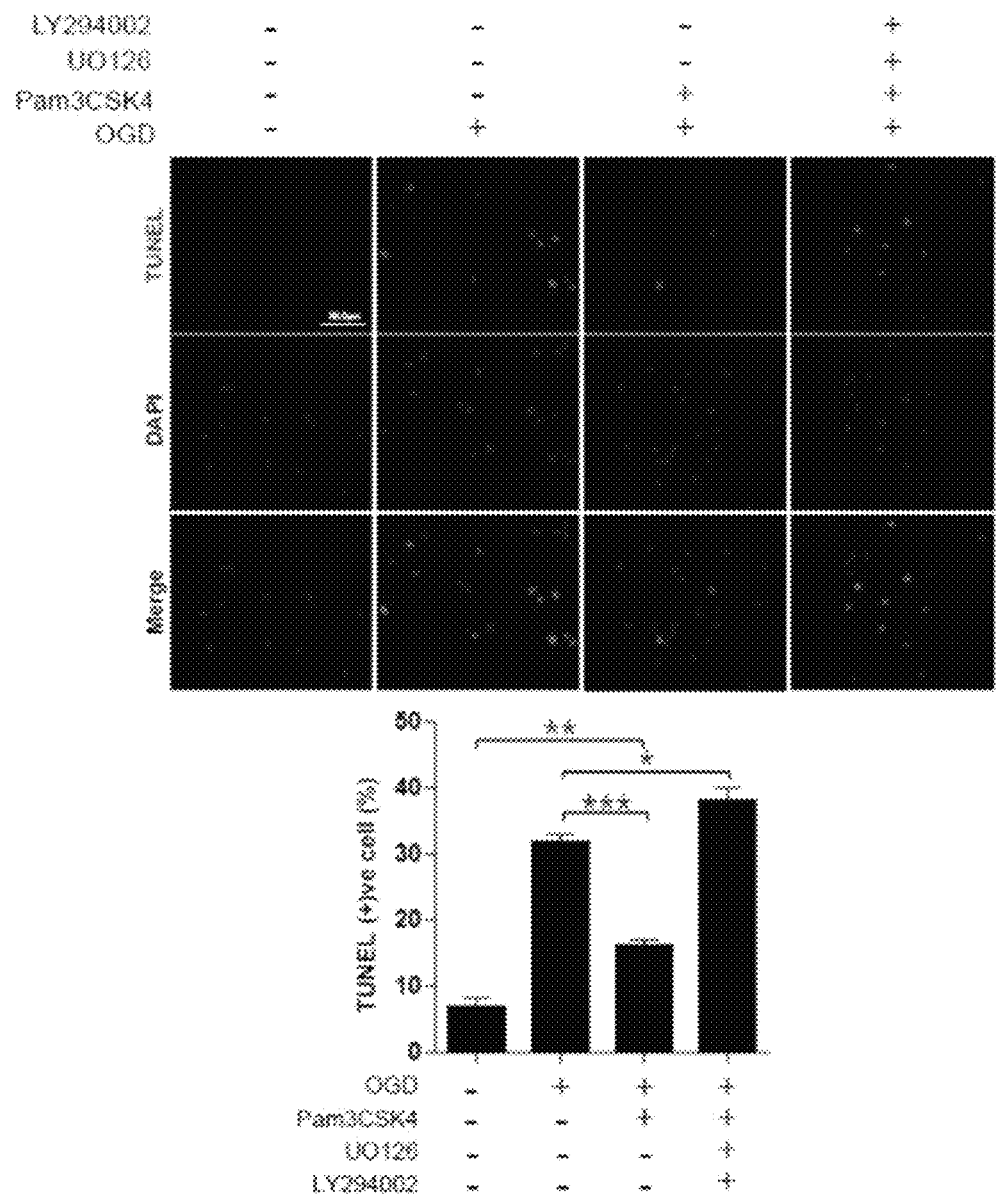

As a result, it was confirmed that, as shown in FIG. 4, the OLs from the TLR2 knockout mouse showed a significant increase in TUNEL staining in accordance with OGD compared to those from the wild type mouse. That is, the OLs from the TLR2 knockout mouse were found to be more vulnerable to OGD than those from the wild type mouse. Meanwhile, as shown in FIG. 5, it was also confirmed that the treatment with TLR2 agonist, Pam3CSK4, reduced the extent of OGD-induced OL death.

EXAMPLE 3

Western Blot Analysis

Animals were injected with ET-1, and brain tissues obtained at $7^{th}$ day after ET-1 injection were homogenized in ice-cold lysis buffer containing 20 mM Tris-HCl (pH 7.5), 1 mM EDTA, 5 mM $MgCl_2$, 1 mM dithiothreitol, 0.1 mM phenylmethylsulfonyl fluoride, and protease/phosphatase inhibitor cocktail. Cultured cells were washed with 2 two times, and then, harvested using the same lysis buffer. Tissues or cell lysates were centrifuged at 20,000 g for 20 minutes at a temperature of about 4° C.

Figure 6:
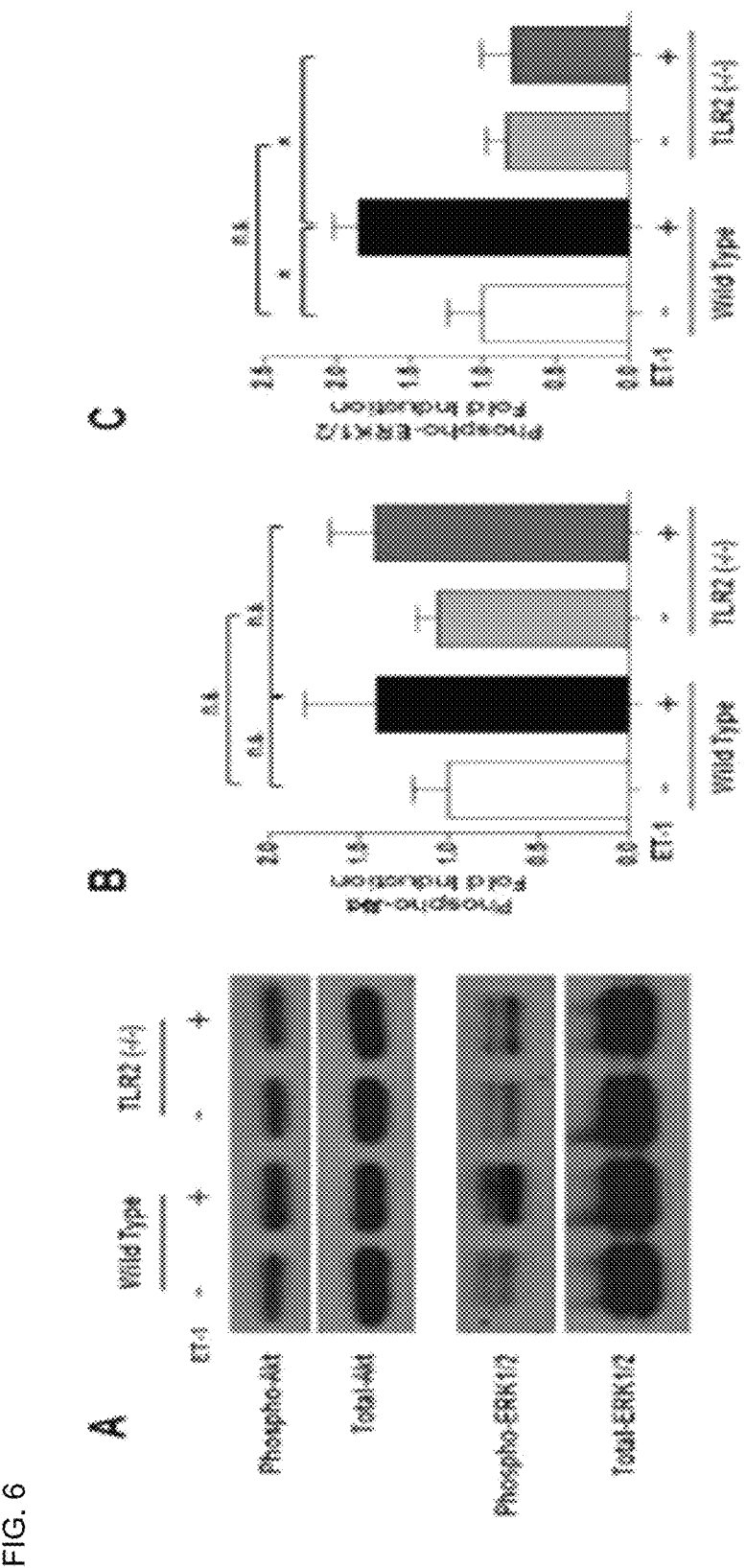
FIG. 6 shows the results of western blot analysis obtained by comparing ERK1/2 phosphorylation in TLR2 knockout mouse to that in the wild type mouse.

Then, the concentration of supernatant proteins was analyzed according to the Bradford assay. Equal amounts of proteins were separated by SDS-PAGE using 10% gel or a graded series of 4% to 20% gels, and then, transferred to PVDF membranes (Immobilion-P; Millipore). The membranes were blocked at room temperature for about 1 hour with 5% nonfat milk or bovine serum albumin, and then, incubated with following antibodies; anti-phospho ERK1/2 (rabbit monoclonal; 1:1000; Cell signaling), anti-total ERK1/2 (rabbit monoclonal; 1:1000; Cell signaling), anti-phospho Akt (rabbit monoclonal; 1:1000; Cell signaling), anti-total Akt (rabbit monoclonal; 1:1000; Cell signaling), and anti-β actin (1:20,000). After washing, the membranes were incubated at room temperature for about 2 hours with horseradish peroxidase-conjugated secondary antibodies. Finally, the membranes were visualized using an enhanced chemiluminescence (ECL) detection agent. As a result, it was confirmed that, as shown in FIG. 6, ERK1/2 phosphorylation was significantly reduced in the TLR2 (−/−) knockout mouse compared to that in the wild type mouse.

EXAMPLE 4

RT-PCR and Quantitative Real Time RT-PCR(qRT-PCR)

Total RNAs were extracted from culture cells or ET-1 injected brain tissues using Trizol (Gibco, Gaithersburg MD). RNAs obtained therefrom were quantified by a spectrophotometer at a wavelength of 260 nm. 1 μg of RNA was reverse transcribed to cDNA using a standard RT protocol. 1 μl of cDNA was added to PCR-reaction premix (GenDE-POT, Barker, Tex., USA) with 10 pM corresponding primer pairs. Here, following primers were used for quantitative RT-PCR (qRT-PCR).

```
18S ribosomal,
                            (forward, SEQ ID NO: 1)
 5'-CGGCTACCACATCCAAGGAA-3', (reverse, SEQ ID NO: 2)
 5'-TGCTGGCACCAGACTTGCCCTC-3', TLR2,
                            (forward, SEQ ID NO: 3)
 5'-CTCCCACTTCAGGCTCTTTG-3', (reverse, SEQ ID NO: 4)
 5'-TCAGGAACTGGGTGGAGAAC-3', TNF-a,
                            (forward, SEQ ID NO: 5)
 5'-AGCAAACCACCAAGTGGAGGA-3', (reverse, SEQ ID NO: 6)
 5'-GCTGGCACCACTAGTTGGTTGT-3', IL-1β,
                            (forward, SEQ ID NO: 7)
 5'-TTGTGGCTGTGGAGAAGCTGT-3', (reverse, SEQ ID NO: 8)
 5'-AACGTCACACACCAGCAGGTT-3', IL-6,
                            (forward, SEQ ID NO: 9)
 5'-TCCATCCAGTTGCCTTCTTGG-3', (reverse, SEQ ID NO: 10)
 5'-CCACGATTTCCCAGAGAACATG-3'.
```

The qRT-PCR was performed according to the protocol of the Applied Biosystem SYBR Green PCR kit using 7500 Real-time PCR system (Applied Biosystems, Foster City, Calif., USA). Amplification was performed with 34 cycles consisting of 30 seconds at a temperature of about 94° C., 31 seconds at a temperature in a range of about 55° C. to about 64° C., and 60 seconds at a temperature of about 72° C. The CT values were quantified by the Applied Biosystem 7500, and the standardization thereof was carried out using 18s ribosomal RNA as an internal control.

Figure 7:
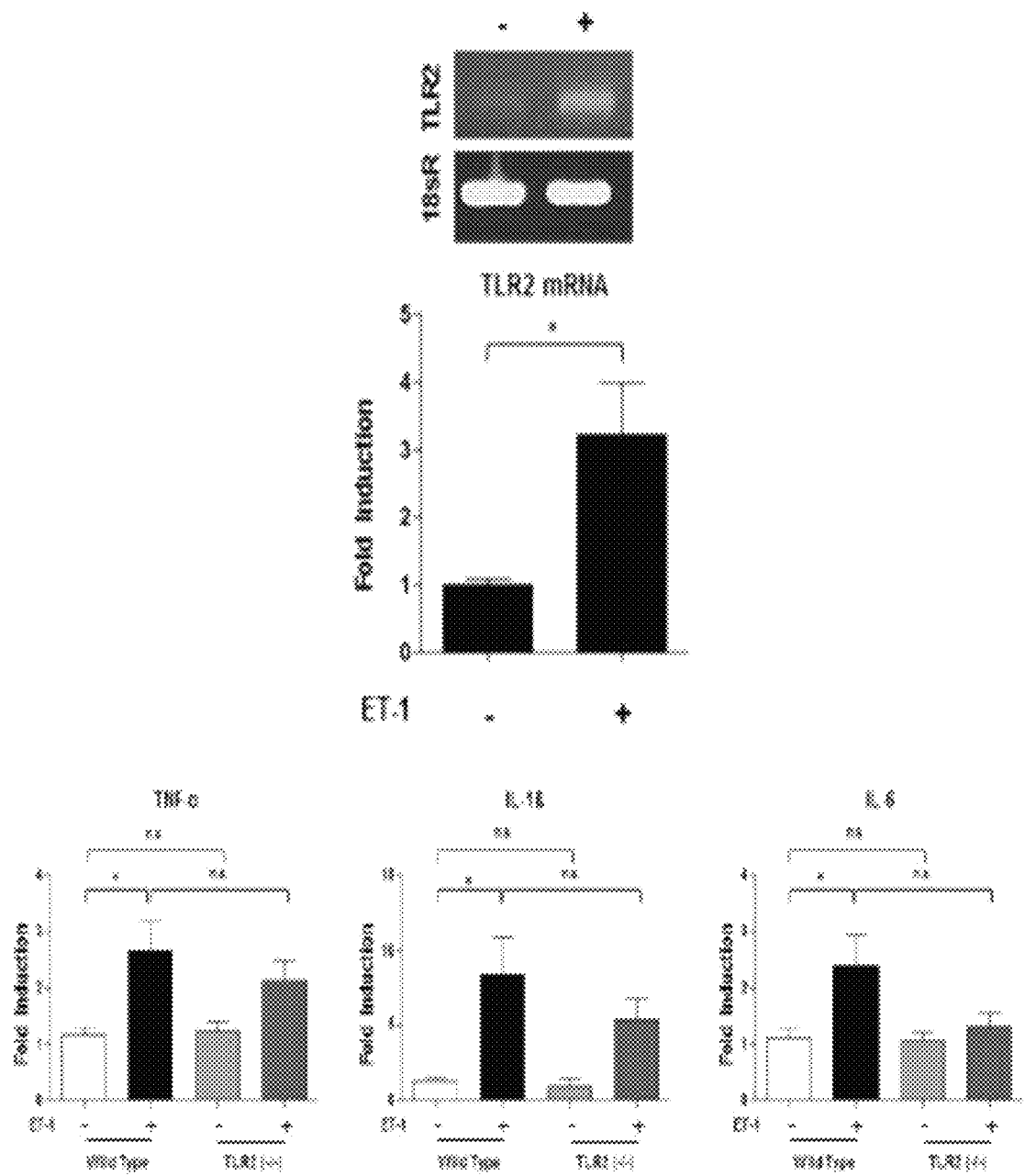
FIG. 7 shows the results of RT-PCR and quantitative real time RT-PCR(qRT-PCR) analysis showing extents of TLR2 and inflammatory cytokines, such as TNF-a, IL-1β, and IL-6 at the lesion area of the wile type mouse where the ischemic demyelinating is induced after the ET-1 injection.

As a result, it was confirmed that, as shown in FIG. 7, the expression of mRNA of TLR2 was significantly increased at the lesion area after the ET-1 injection in the wild type mouse, and in addition, there was no significant differences in the amount of inflammatory cytokines, such as TNF-a, IL-β, and IL-6, between the TLR2 (−/−) knockout mouse and the wild type mouse.

It should be understood that the exemplary embodiments described therein should be considered in a descriptive sense only and not for purposes of limitation. Descriptions of the features or aspects within each embodiment should typically be considered as being available for other similar features or aspects in other embodiments. While one or more exemplary embodiments have been described with reference to the figures, it will be understood by those of ordinary skill in the art that various changes in form and details may be made therein without departing from the spirit and scope of the inventive concept as defined by the following claims

INDUSTRIAL APPLICABILITY

The present invention discloses a biomarker for detecting white matter stroke, including a toll-like receptor 2 (TLR2). The disclosure may be applied to a kit for diagnosing white matter stroke using TLR2-specific molecules, and by determining extent of the TLR2 expression, the disclosure may be also used for a therapeutic agent to prevent and treat white matter stroke and a method of treating white matter stroke.

The invention claimed is:

1. A method of screening a therapeutic agent for ischemic white matter stroke accompanied by oligodendrocyte damage, the method comprising:

preparing and purifying primary oligodendrocyte cultures from mouse cortices of a wild type mouse and a toll-like receptor 2 (TLR2) knockout mouse;

subjecting each of the purified oligodendrocyte cultures of the wild type mouse and the TLR2 knockout mouse to oxygen-glucose deprivation;

measuring and comparing oligodendrocyte (OL) death in the purified OL cultures using lactate dehydrogenase (LDH) assay, wherein the OL death is increased in cultures of the TLR2 knockout mouse OL as compared to the wild type OL cultures;

treating the purified oligodendrocyte cultures of the TLR2 knockout mouse with a candidate compound and measuring the OL death; and determining that the candidate compound is the therapeutic agent for the ischemic white matter stroke if the OL death in the purified OL cultures treated with the candidate compound is lower as compared to the purified OL cultures without being treated the candidate compound.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Forward primer for 18S ribosomal

<400> SEQUENCE: 1
cggctaccac atccaaggaa					20

<210> SEQ ID NO 2
<211> LENGTH: 22
<212> TYPE: DNA
<213> ORGANISM: Artificial Sequence
<220> FEATURE:
<223> OTHER INFORMATION: Backward primer for 18S ribosomal

<400> SEQUENCE: 2
tgctggcacc agacttgccc tc				22

<210> SEQ ID NO 3
<211> LENGTH: 20
<212> TYPE: DNA
<213> ORGANISM: Artificial Sequence
<220> FEATURE:
<223> OTHER INFORMATION: Forward primer for TLR2

<400> SEQUENCE: 3
ctcccacttc aggctctttg					20

<210> SEQ ID NO 4
<211> LENGTH: 20
<212> TYPE: DNA
<213> ORGANISM: Artificial Sequence
<220> FEATURE:
<223> OTHER INFORMATION: Backward primer for TLR2

<400> SEQUENCE: 4
tcaggaactg ggtggagaac					20

<210> SEQ ID NO 5
<211> LENGTH: 21
<212> TYPE: DNA
<213> ORGANISM: Artificial Sequence
<220> FEATURE:
<223> OTHER INFORMATION: Forward primer for TNF-a

<400> SEQUENCE: 5
agcaaaccac caagtggagg a					21

<210> SEQ ID NO 6
<211> LENGTH: 22
<212> TYPE: DNA
<213> ORGANISM: Artificial Sequence
<220> FEATURE:
<223> OTHER INFORMATION: Backward primer for TNF-a

<400> SEQUENCE: 6
gctggcacca ctagttggtt gt				22

<210> SEQ ID NO 7
<211> LENGTH: 21
<212> TYPE: DNA
<213> ORGANISM: Artificial Sequence

```
<220> FEATURE:
<223> OTHER INFORMATION: Forward primer for IL-1beta

<400> SEQUENCE: 7
ttgtggctgt ggagaagctg t                                              21

<210> SEQ ID NO 8
<211> LENGTH: 21
<212> TYPE: DNA
<213> ORGANISM: Artificial Sequence
<220> FEATURE:
<223> OTHER INFORMATION: Backward primer for IL-1beta

<400> SEQUENCE: 8
aacgtcacac accagcaggt t                                              21

<210> SEQ ID NO 9
<211> LENGTH: 21
<212> TYPE: DNA
<213> ORGANISM: Artificial Sequence
<220> FEATURE:
<223> OTHER INFORMATION: Forward primer for IL-6

<400> SEQUENCE: 9
tccatccagt tgccttcttg g                                              21

<210> SEQ ID NO 10
<211> LENGTH: 22
<212> TYPE: DNA
<213> ORGANISM: Artificial Sequence
<220> FEATURE:
<223> OTHER INFORMATION: Backward primer for IL-6

<400> SEQUENCE: 10
ccacgatttc ccagagaaca tg                                             22
```